US009022942B2

(12) United States Patent
Quinn et al.

(10) Patent No.: US 9,022,942 B2
(45) Date of Patent: May 5, 2015

(54) SYSTEMS AND METHODS FOR MEASURING ARTERIAL STIFFNESS

(75) Inventors: David E. Quinn, Auburn, NY (US);
Matt Kinsley, Liverpool, NY (US);
Tyson B. Whitaker, Arden, NC (US);
John D. Seller, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 395 days.

(21) Appl. No.: 13/471,588

(22) Filed: May 15, 2012

(65) Prior Publication Data
US 2012/0226173 A1    Sep. 6, 2012

Related U.S. Application Data

(63) Continuation of application No. 12/787,220, filed on May 25, 2010, now Pat. No. 8,197,414.

(51) Int. Cl.
| A61B 5/02 | (2006.01) |
| A61B 5/022 | (2006.01) |
| A61B 5/021 | (2006.01) |
| A61B 5/0225 | (2006.01) |
| A61B 5/11 | (2006.01) |
| A61B 5/00 | (2006.01) |

(52) U.S. Cl.
CPC ............. *A61B 5/02225* (2013.01); *A61B 5/022* (2013.01); *A61B 5/021* (2013.01); *A61B 5/02007* (2013.01); *A61B 5/0225* (2013.01); *A61B 5/1107* (2013.01); *A61B 5/6824* (2013.01)

(58) Field of Classification Search
USPC .......... 600/481, 485, 490, 493–496, 500–503
See application file for complete search history.

(56) References Cited

U.S. PATENT DOCUMENTS

| 5,497,778 | A | 3/1996 | Hon |
| 5,653,241 | A | 8/1997 | Harada et al. |
| 6,331,159 | B1 | 12/2001 | Amano et al. |
| 6,712,768 | B2 | 3/2004 | Ogura et al. |
| 6,733,461 | B2 | 5/2004 | Bratteli |
| 6,793,628 | B2 | 9/2004 | Ogura et al. |
| 6,814,705 | B2 | 11/2004 | Kawaguchi |
| 6,976,966 | B2 | 12/2005 | Narimatsu |
| 6,994,675 | B2 | 2/2006 | Sharrock |
| 7,468,037 | B2 | 12/2008 | Illyes et al. |
| 2002/0183627 | A1* | 12/2002 | Nishii et al. .................. 600/485 |
| 2003/0040675 | A1* | 2/2003 | Sharrock ....................... 600/490 |
| 2004/0024323 | A1 | 2/2004 | Kulik |

(Continued)

OTHER PUBLICATIONS

Alpert, B.S. "Clinical evaluation of the Welch Allyn SureBP algorithm for automated blood pressure measurement" *Blood Pressure Monitoring* 12(4):215-218 (2007).
Gelido, G. et al. "Arterial pressure measurement: Is the envelope curve of the oscillometric method influenced by arterial stiffness?" *J. Phys.: Conf. Ser.* 90:012053, 8 pages (2007).
MacKenzie, I.S. et al. "Assessment of arterial stiffness in clinical practice" *Q.J. Med.* 95:67-74 (2002).

(Continued)

*Primary Examiner* — Michael D'Angelo

(57) ABSTRACT

Disclosed herein is a system for monitoring a patient that includes a cuff configured to inflate to at least partially occlude an artery of the patient and a cuff controller configured to control inflation and deflation of the cuff. The system also includes a sensor configured to receive a signal associated with the at least partially occluded artery and generate an output signal based on the received signal. Also included is a signal analysis module configured to receive the output signal and determine a first hemodynamic parameter based on a first set of data obtained during inflation of the cuff and a second set of data obtained during deflation of the cuff.

19 Claims, 3 Drawing Sheets

(56) References Cited

U.S. PATENT DOCUMENTS

| | | |
|---|---|---|
| 2004/0077959 A1 | 4/2004 | Narimatsu |
| 2006/0229517 A1 | 10/2006 | Lin et al. |
| 2007/0123784 A1 | 5/2007 | Hersh et al. |
| 2008/0243009 A1 | 10/2008 | Hersh et al. |
| 2009/0221924 A1* | 9/2009 | Friedman et al. ............ 600/490 |

OTHER PUBLICATIONS

McLaughlin, J. et al. "Piezoelectric sensor determination of arterial pulse wave velocity" *Physiol. Meas.*, 24:693-702 (2003).

International Search Report and Written Opinion issued in International Patent Application No. PCT/US2011/27534, dated Sep. 28, 2011, 8 pages.

* cited by examiner

SYSTEMS AND METHODS FOR MEASURING ARTERIAL STIFFNESS

CROSS-REFERENCE TO RELATED APPLICATION

This application is a continuation of U.S. application Ser. No. 12/787,220, filed May 25, 2010, the entirety of which is incorporated herein by reference.

TECHNICAL FIELD

This application is directed to systems and methods for monitoring a patient, and in particular, to non-invasive measurement of arterial stiffness.

BACKGROUND

Arterial stiffness is an important physiological measurement for the assessment of cardiovascular health. Elevated arterial stiffness can raise arterial pressure and negatively alter flow dynamics and can also impact cardiac performance and coronary perfusion. Some methods have been developed to estimate arterial stiffness. These methods, however, can be expensive, complicated, invasive and difficult to perform. Accordingly, an improved, non-invasive, user-friendly, easy, low-cost solution is needed to facilitate routine screening of arterial stiffness.

SUMMARY

A first aspect of the present disclosure includes a system for monitoring a patient having an external cuff configured to inflate to at least partially occlude an artery of the patient and a cuff controller configured to control inflation and deflation of the cuff. The system also includes a sensor configured to receive a signal associated with the at least partially occluded artery and generate an output signal based on the received signal, and a signal analysis module configured to receive the output signal and determine a first hemodynamic parameter based on a first set of data obtained during inflation of the cuff and a second set of data obtained during deflation of the cuff.

In some embodiments of the system, the sensor may include a pressure sensor and/or may be configured to operate with an oscillometric method. In one version, the first set of data may include a first oscillometric pulse envelope curve and the second set of data may include a second oscillometric pulse envelope curve. In some embodiments, the signal analysis module may compare the first oscillometric pulse envelope curve to the second oscillometric pulse envelope curve and determine a difference. The difference may be related to the first hemodynamic parameter.

In some versions, the signal analysis module may determine a peak of the first oscillometric pulse envelope curve and a peak of the second oscillometric pulse envelope curve. According to one aspect, the signal analysis module may compare the peaks and determine a difference. This difference may be related to the first hemodynamic parameter. In some embodiments, the peak of the second oscillometric pulse envelope curve may substantially correspond to a mean arterial pressure. According to some embodiments, the first hemodynamic parameter may be arterial stiffness.

In some embodiments, the signal analysis module may determine a second hemodynamic parameter based on the output signal. In some versions, the signal analysis module uses the first hemodynamic parameter in determining the second hemodynamic parameter. In one feature, the second hemodynamic parameter may be blood pressure.

A second aspect of the present disclosure includes a method of determining a hemodynamic parameter of a patient that includes providing a cuff configured to at least partially occlude a vessel of the patient. The method includes inflating the cuff over an inflation period and obtaining a first set of data from the cuff during at least a portion of the inflation period. The method also includes deflating the cuff over a deflation period and obtaining a second set of data during at least a portion of the deflation period. The method further includes determining a first hemodynamic parameter based on the first set of data and the second set of data.

Some versions of the method may further include obtaining a first oscillometric pulse envelope curve from the first set of data and obtaining a second oscillometric pulse envelope curve from the second set of data. In some embodiments, the first hemodynamic parameter may be determined by comparing a first feature of the first oscillometric pulse envelope curve to a second feature of the second oscillometric pulse envelope curve. The first feature may include a peak of the first oscillometric pulse envelope curve and the second feature may include a peak of the second oscillometric pulse envelope curve. According to some embodiments, the first hemodynamic parameter may be arterial stiffness.

In some embodiments, the method may also include determining a second hemodynamic parameter. The second hemodynamic parameter may be based, at least in part, on the first hemodynamic parameter. In some versions, the second hemodynamic parameter may be blood pressure.

Additional objects and advantages of the present disclosure will be set forth in part in the description which follows, and in part will be obvious from the description, or may be learned by practice of the present disclosure. The objects and advantages of the present disclosure will be realized and attained by means of the elements and combinations particularly pointed out in the appended claims.

It is to be understood that both the foregoing general description and the following detailed description are exemplary and explanatory only and are not restrictive of the present disclosure, as claimed.

The accompanying drawings, which are incorporated in and constitute a part of this specification, illustrate several embodiments of the present disclosure and together with the description, serve to explain the principles of the present disclosure.

DETAILED DESCRIPTION

Reference will now be made in detail to the present embodiments (exemplary embodiments) of the invention, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit, unless specifically stated otherwise. Also, the use of the term "portion" may include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Figure 1:
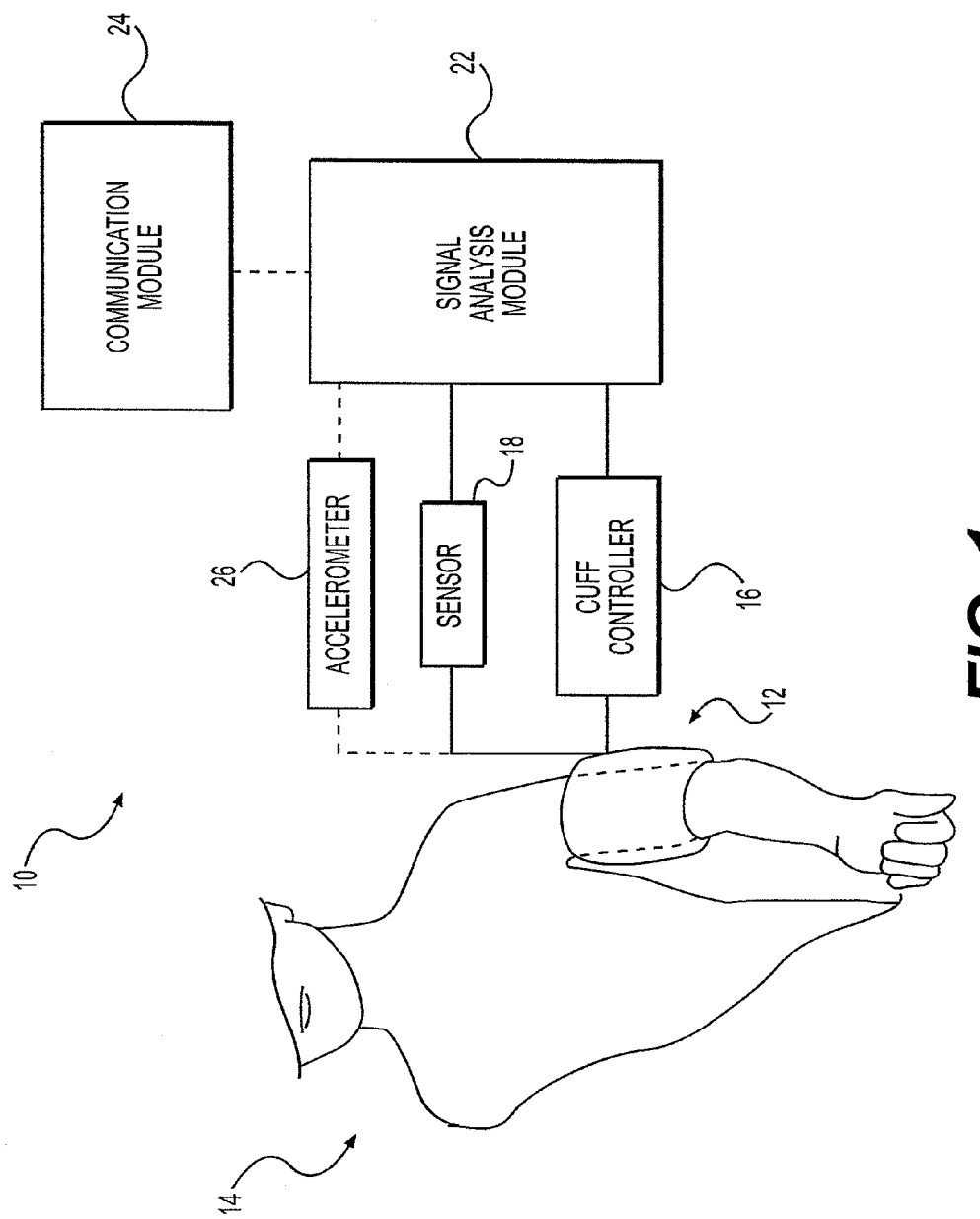
FIG. 1 illustrates a monitoring system, according to an exemplary embodiment.

Disclosed herein are patient monitoring systems and methods of using such systems. FIG. 1 illustrates a system 10, according to an exemplary embodiment of the present disclosure. System 10 can be configured to monitor a patient, and in some embodiments, to determine a hemodynamic parameter of the patient.

System 10 can include a cuff 12 configured to at least partially occlude the movement of blood through a vessel of patient 14. In some embodiments, cuff 12 can be configured to completely occlude an artery of patient 14. Although shown in FIG. 1 surrounding the upper arm of patient 14, cuff 12 may be adapted for placement on any suitable part of patient 14, including, for example, a wrist, a finger, an upper thigh, or an ankle. In addition, one or more cuffs 12 could be placed at different locations about patient 14 for use with system 10.

Cuff 12 can include an inflatable device, wherein the pressure or volume within cuff 12 may be controlled by a cuff controller 16 operably associated with cuff 12. Cuff controller 16 can include a pump or similar device to inflate cuff 12. For example, cuff controller 16 could supply cuff 12 with a fluid to increase the pressure or volume of cuff 12. In other embodiments, cuff controller 16 could include mechanical, electrical, or chemical devices configured to control vessel occlusion of patient 14 via cuff 12.

System 10 can further include a sensor 18 configured to receive a signal associated with patient 14. In some embodiments, sensor 18 can be configured to receive a signal associated with an at least partially occluded vessel of patient 14. Such an input signal can arise from blood movement through a partially occluded vessel or from a signal associated with an occluded blood vessel. Sensor 18 could sample multiple times at various intervals. In yet other embodiments, sensor 18 could provide an indication of blood vessel movement, such as, for example, oscillations arising from vascular expansion or contraction. For example, in an oscillometric method, sensor 18 could be configured to detect a pressure or volume of cuff 12 that may vary periodically with the cyclic expansion and contraction of an artery of patient 14.

In some embodiments, sensor 18 could detect a volume or a pressure associated with cuff 12. For example, sensor 18 could include a pressure sensor and may be located within or about cuff 12. System 10 could further operate with a plurality of sensors 18, and may include a high-resolution sensor or pneumatic sensor designed to operate in conjunction with cuff 12.

Sensor 18 can further be configured to generate an output signal. The output signal may be generated based on an input signal received from patient 14. In one aspect, the output signal can include a representation of an input signal associated with cuff 12 and/or patient 14.

As shown in FIG. 1, system 10 can include a signal analysis module 22. Signal analysis module 22 may be configured to analyze one or more signals using one or more processors. Such analysis may be based on the output signal of sensor 18. For example, signal analysis module 22 can include one or more filters configured to filter a signal associated with sensor 18 or cuff controller 16. Such filters can include band-pass, band-stop, high-pass, or low-pass filters.

In some embodiments, signal analysis module 22 may determine one or more hemodynamic parameters. A hemodynamic parameter can include an indication of cardiac or vascular health, such as, for example, an indication of cardiac, circulatory, or vascular functionality. Specifically, a hemodynamic parameter can include a heart rate, a blood pressure, an arterial stiffness, an aortic index, an augmentation index, reflected wave ratio, or an indication of treatment. Blood pressure can include systolic, diastolic, or mean arterial pressure. An indication of treatment can include a parameter reflecting the effect of a drug treatment, or one or more treatments of a disease state.

In some embodiments, a hemodynamic parameter can be determined based on a first set of data obtained during inflation of cuff 12 and a second set of data obtained during deflation of cuff 12, as explained below in detail. The first or second sets of data can include various data associated with a signal waveform related to patient 14 and/or cuff 12, and may include amplitude, frequency, morphology, feature, or mathematically derived data. Data can be derived from a derivative, integration, or frequency analysis, such as, for example, a fast-Fourier transform. Data may also be derived from various algorithms, including curve fitting, neural network, filtering, smoothing, or data processing. In other embodiments, a hemodynamic parameter can be determined based on a suprasystolic measurement or a combination of inflation, deflation, and suprasystolic measurements.

System 10 can further include an accelerometer 26 to detect movement. Accelerometer 26 can be configured to detect movement in one, two, or three dimensions. For example, accelerometer 26 could be used to detect movement of patient 14 or movement of the arm of patient 14.

A signal arising from accelerometer 26 could be used to provide additional information to another module. For example, if movement of patient 14 is sufficient to interfere with sensor 18, a signal from accelerometer 26 may be transmitted to signal analysis module 22 to halt the pressure cycle. In addition, a signal from accelerometer 26 may be transmitted to signal analysis module 22 to cancel or reset a calculation. Data obtained from sensor 18 could be combined with data from accelerometer 26 to determine if an irregular signal may be caused by a motion artifact. Various data from accelerometer 26 may be processed to provide additional data to determine one or more hemodynamic parameters.

System 10 can further include a communication module 24 configured to provide communication to patient 14 or one or more operators. For example, communication module 24 could include a display configured to display one or more hemodynamic parameters. In other embodiments, communication module 24 could include a transmitter configured to transmit data to a remote location. Communication module 24 may further include audio output to communicate with patient 14 and/or an operator of system 10.

In addition to the components outlined above, system 10 may include various other components as required, such as, for example, a memory, a power source, and a user input. One or more components described herein may be combined or may be separate and operate with wireless or wired communication links. Moreover, the various components of system 10 could be integrated into a single processing unit or may operate as separate processors. In operation, one or more processors can be configured to operate in conjunction with one or more software programs to provide the functionality of system 10.

Figure 2:
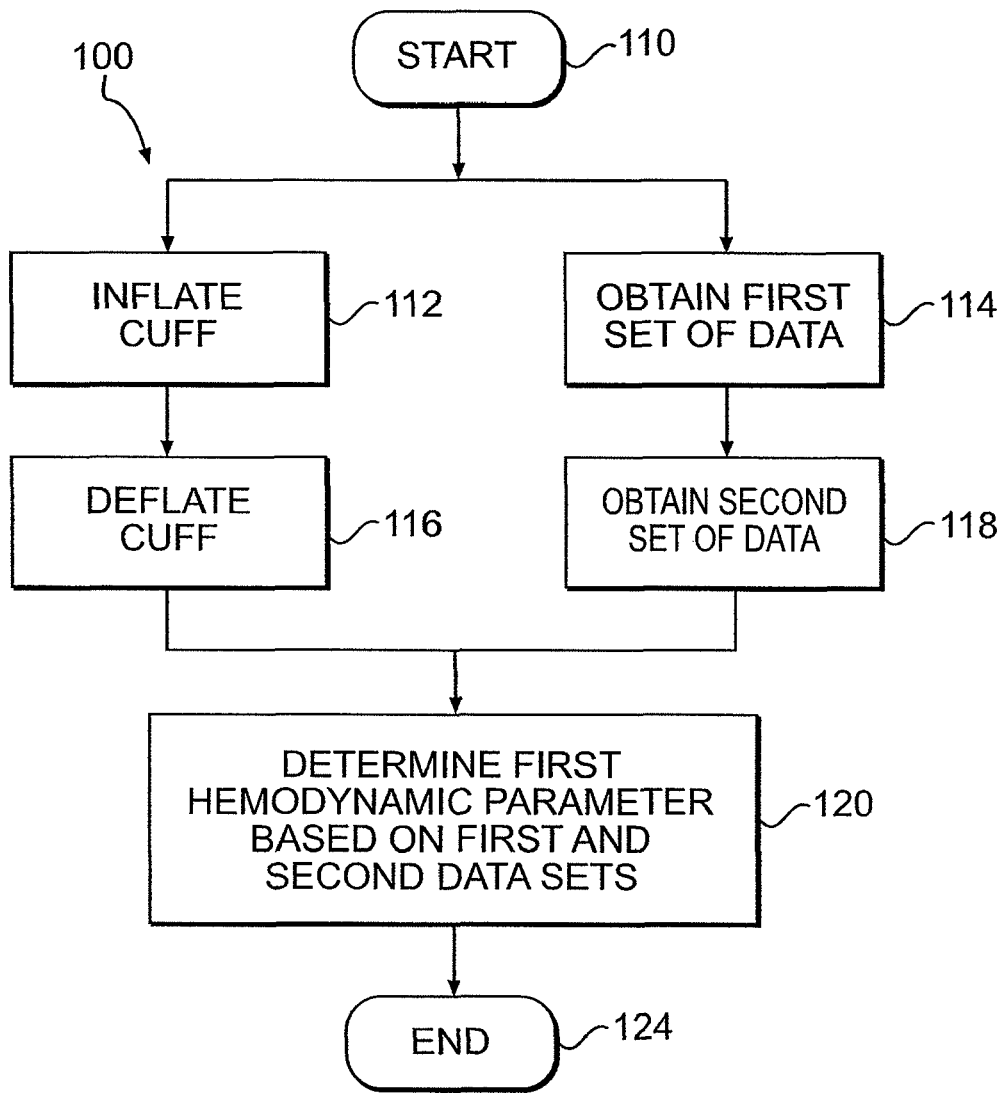
FIG. 2 illustrates a first flow chart, according to an exemplary embodiment.

FIG. 2 illustrates a flow chart of an exemplary embodiment according to the present disclosure. As described above with regard to FIG. 1, various modules can include one or more hardware components and one or more software components that operate to control an operation of system 10. Each step described below can be understood as corresponding to one or more computational instructions. These computational instructions can operate based on hardware and/or software components of system 10, and may operate on one or more processors.

FIG. 2 includes a process 100 according to an exemplary embodiment of the present disclosure. Step 110, labeled "Start," may include one or more steps required to initiate an operation of system 10. For example, system 10 may be turned on, a calibration protocol may be started, a cuff may be placed about a patient's arm, an operator may enter information to identify a patient, or information could be extracted from a database. Further, various components of system 10 may be calibrated or tested to ensure proper functioning. These operations could include a check of cuff integrity, a determination of whether sufficient power is available, a calibration of one or more sensors, or confirmation of proper processor functioning. Also, other information may be entered into system 10, such as a patient identification, weight, gender, height, or other suitable data.

After system 10 has completed start 110, cuff controller 16 may operate to inflate cuff 12 (Step 112) over an inflation period. In some embodiments, Step 112 could be initiated as part of Step 110. During inflation, sensor 18 may detect one or more signals, as discussed above, and generate one or more corresponding output signals to be received by signal analysis module 22. Accordingly, signal analysis module 22 may obtain a first set of data (Step 114) during at least a portion of the inflation period. Cuff controller 16 may then operate to deflate cuff 12 (Step 116) over a deflation period, and in some embodiments, sensor 18 may detect one or more signals and generate one or more corresponding output signals to be received by signal analysis module 22. Accordingly, signal analysis module 22 may obtain a second set of data (Step 118) during at least a portion of the deflation period. Once the second set of data has been obtained, signal analysis module 22 may determine a first hemodynamic parameter based on the first and second data sets (Step 120).

Following Step 120, process 100 may end (Step 124). Termination of process 100 can include display of one or more hemodynamic parameters, commencement of another process, and/or power shut-down.

Figure 3:
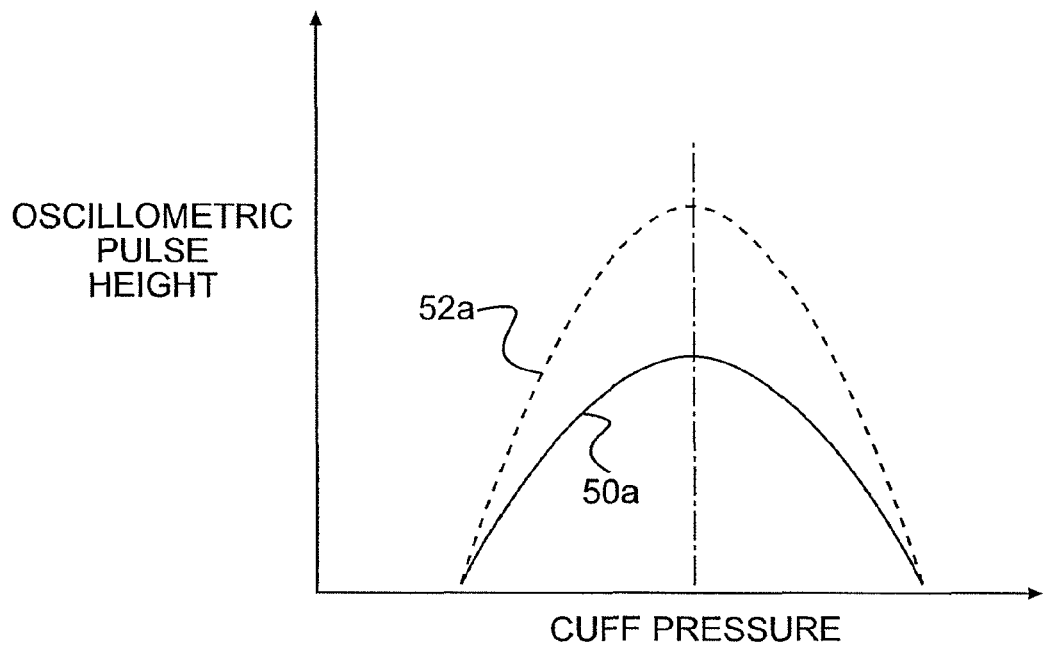
FIG. 3 illustrates exemplary oscillometric pulse envelope curves under conditions of minimal arterial stiffness.
Figure 4:
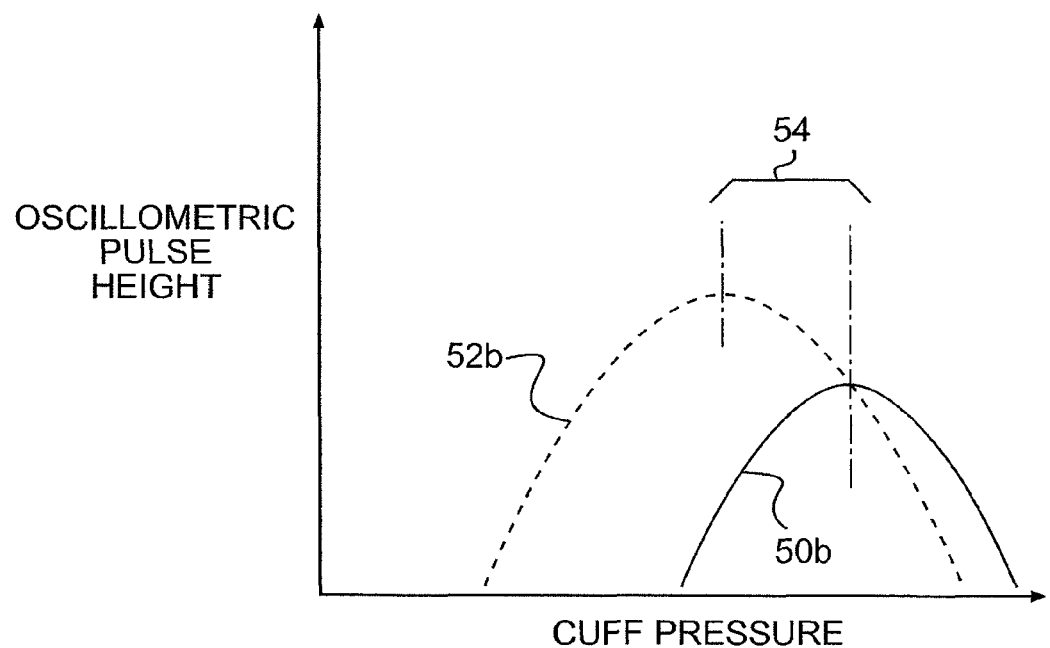
FIG. 4 illustrates exemplary oscillometric pulse envelope curves under conditions of increased arterial stiffness.

In some embodiments, the first and second sets of data may comprise oscillometric pulse data. For example, the first set of data may comprise a first oscillometric pulse envelope curve, and the second set of data may comprise a second oscillometric pulse envelope curve. FIGS. 3 and 4 illustrate exemplary plots of first oscillometric pulse envelope curve 50a,b and second oscillometric pulse envelope curve 52a,b.

The first oscillometric pulse envelope curve may differ from the second oscillometric pulse envelope curve as a function of the stiffness of an artery of patient 14. The first oscillometric pulse envelope curve is based on data obtained during the inflation period. During the inflation period, the amount of force required to compress the artery may be dependent on a combination of the cuff occlusion efficiency and the amount of force required to overcome any hoop strength of the arterial wall. An increase in the stiffness of the arterial wall can cause an increase in the hoop strength of the arterial wall. In contrast, the second oscillometric pulse envelope curve is based on data obtained during the deflation period. During the deflation period, the artery has already been compressed, so the force required to collapse the artery does not affect the oscillometric pulse envelope curve. Thus, increased stiffness of the arterial wall creates a difference between the first oscillometric pulse envelope and the second oscillometric pulse envelope curve.

For example, FIG. 3 depicts a first pulse envelope curve 50a obtained during inflation and a second pulse envelope curve 52a obtained during deflation, both measured from an artery having minimal stiffness. Here, the peak of the first pulse envelope curve 50a occurs at approximately the same cuff pressure as the peak of the second pulse envelope curve 52a. In contrast, FIG. 4 depicts first and second pulse envelope curves measured from an artery having increased stiffness. The increased stiffness results in a shift of the first pulse envelope curve 50b, which was obtained during inflation, with respect to the second pulse envelope curve 52b, which was obtained during deflation. This shift indicates that a greater amount of pressure is required to compress the artery during inflation than during deflation. Accordingly, the peak of the first pulse envelope curve 50b occurs at a higher cuff pressure than the peak of the second pulse envelope curve 52b. Furthermore, the value of the difference 54 between cuff pressure at the peak of the first envelope curve and cuff pressure at the peak of the second envelope curve may indicate the severity of the arterial stiffness.

In some embodiments, signal analysis module 22 may determine a first hemodynamic parameter based on comparing the first oscillometric pulse envelope curve to the second oscillometric pulse envelope curve. As discussed above, signal analysis module 22 may compare, for example, amplitude, frequency, morphology, feature, or mathematically derived data of the oscillometric data. In some embodiments, signal analysis module 22 may identify the peaks of the first and second oscillometric pulse envelope curves and determine the difference 54, if any, in cuff pressure between the two peaks. Thus, signal analysis module 22 may determine atrial stiffness based on the difference 54 between the peaks of the first and second oscillometric pulse envelope curves.

In some embodiments, after determining a first hemodynamic parameter, signal analysis module 22 may then determine a second hemodynamic parameter. The second hemodynamic parameter may be determined based on the first set of data, the second set of data, an additional set of data, the first hemodynamic parameter, or combinations thereof. For example, signal analysis module 22 may be configured to calculate arterial stiffness and blood pressure. Generally, blood pressure measurements from an oscillometric reading can be influenced by arterial stiffness. To account for this, in some embodiments of the present disclosure, signal analysis module 22 may use a value of arterial stiffness determined to modify or correct blood pressure measurements by accounting for arterial stiffness.

The order of the inflation and deflation periods may vary. For example, in some embodiments, a first set of data may be obtained during an inflation period that occurs after the deflation period during which a second set of data was obtained. Further, in some embodiments, the inflation and deflation periods may occur in close time proximity to each other, but not necessarily consecutively. For example, in some embodiments, the inflation and deflation periods may be separated by one or more other phases of differing cuff pressure and/or duration, such as, for example, a suprasystolic phase.

The duration of the inflation and deflation periods may also vary. In some embodiments the inflation and deflation periods may occur for predetermined amounts of time. Inflation and deflation may also be configured to operate until predetermined pressures are reached. In some embodiments, inflation and deflation may operate until a determination has been made that sufficient information has been obtained. For example, during inflation or deflation, sensor 18 may detect signals for determining if sufficient information has been obtained. The source of this data may be different from the source of the first and second sets of data.

In some embodiments, an algorithm for determining termination of inflation or deflation may use oscillometric pulse data obtained during the inflation or deflation periods. The data may be analyzed in real time until such a point that an algorithm deems the data sufficient for a reading determination. Such data can relate to the maturity of the pulse envelope or the amount of envelope found during inflation. The collected pulse data can be filtered and/or conditioned. In other embodiments, a model curve can be fit to the data. In yet other embodiments, data can be submitted to a trained network of mathematical routines. Such analysis can be used to determine a systolic pressure or a diastolic pressure.

For example, the SureBP algorithm could be used to determine a systolic pressure. Such an algorithm is described in "Clinical evaluation of the Welch Allyn SureBP algorithm for automated blood pressure measurement," by Bruce Alpert, which is hereby incorporated by reference in its entirety. Such an algorithm can provide an accurate measure of systolic pressure during inflation, whereby the mean error is less than about 1 mmHg and the standard deviation of the mean error is less than about .+-.7 mmHg. In other embodiments, such an algorithm could provide a mean error of less than about 5 mmHg and a standard deviation of less than about .+-.5 mmHg.

In some embodiments, signal analysis module 22 may analyze data being received from sensor 18 in real time and determine when a peak has been reached in an oscillometric pulse envelope curve. When a peak has been reached, signal analysis module 22 may deem sufficient data has been received for determining a hemodynamic parameter and terminate the current inflation or deflation period. For example, only enough data sufficient to identify the peak of the first oscillometric pulse envelope curve and the second oscillometric pulse envelope curve may be necessary to determine arterial stiffness.

If an algorithm determines that sufficient information has not yet been obtained, cuff inflation or deflation can continue until sufficient information has been obtained. One or more safety algorithms could also be used to limit cuff inflation to a maximum pressure.

In some embodiments, inflation may stop upon reaching a mean arterial pressure, a systolic pressure, or a suprasystolic pressure. In some embodiments, cuff pressure can be maintained generally at about a suprasystolic pressure for a period of time. Such maintenance can include minor fluctuations about the target pressure. While suprasystolic pressure is maintained, one or more hemodynamic parameters may be determined. The one or more hemodynamic parameters may be determined using suprasystolic analysis methods. For example, U.S. Patent Application Publication No. 2006/0224070 to Sharrock et al. describes using suprasystolic measurements to determine Augmentation index, cardiac performance and cardiac stroke volume. U.S. Patent Application Publication No. 200/0012411 to Lowe et al. describes using oscillometric techniques to analyze suprasystolic signals. Each of these references is hereby incorporated by reference in their entirety.

Other embodiments of the present disclosure will be apparent to those skilled in the art from consideration of the specification and practice of the disclosure contained herein. It is intended that the specification and examples be considered as exemplary only, with a true scope and spirit of the present disclosure being indicated by the following claims.

We claim:

1. A system for monitoring a patient, comprising:
   a cuff configured to inflate to at least partially occlude an artery of the patient;
   a cuff controller configured to control inflation and deflation of the cuff;
   a sensor configured to receive a signal associated with the at least partially occluded artery and generate an output signal based on the received signal; and
   a signal analysis module configured to receive the output signal and determine a first hemodynamic parameter based on a first set of data obtained during inflation of the cuff and a second set of data obtained during deflation of the cuff;
   wherein the sensor is configured to operate with an oscillometric method and the first set of data comprises a first oscillometric pulse envelope curve and the second set of data comprises a second oscillometric pulse envelope curve.

2. The system of claim 1, wherein the signal analysis module is further configured to compare the first oscillometric pulse envelope curve to the second oscillometric pulse envelope curve and determine a difference.

3. The system of claim 2, wherein the first hemodynamic parameter is related to the difference between the first oscillometric pulse envelope curve and the second oscillometric pulse envelope curve.

4. The system of claim 1, wherein the signal analysis module is further configured to determine a peak of the first oscillometric pulse envelope curve and a peak of the second oscillometric pulse envelope curve.

5. The system of claim 4, wherein the signal analysis module is further configured to compare the peak of the first oscillometric pulse envelope curve to the peak of the second oscillometric pulse envelope curve and determine a difference.

6. The system of claim 5, wherein the first hemodynamic parameter is related to the difference between the peak of the first oscillometric pulse envelope curve and the peak of the second oscillometric pulse envelope curve.

7. The system of claim 4, wherein the peak of the second oscillometric pulse envelope curve substantially corresponds to a mean arterial pressure.

8. The system of claim 1, wherein the first hemodynamic parameter is selected from the group consisting of blood pressure, heart rate, aortic index, augmentation index, reflected wave ratio, and mean arterial pressure.

9. The system of claim 1, wherein the signal analysis module is further configured to determine a second hemodynamic parameter based on the output signal.

10. The system of claim 9, wherein the signal analysis module uses the first hemodynamic parameter in determining the second hemodynamic parameter.

11. The system of claim 1, wherein a third set of data is obtained during a suprasystolic pressure.

12. The system of claim 11, wherein the signal analysis module uses the third set of data to determine arterial stiffness.

13. A method of determining a hemodynamic parameter of a patient, comprising:
- providing a cuff configured to at least partially occlude a vessel of the patient;
- inflating the cuff over an inflation period;
- obtaining a first set of data from the cuff during at least a portion of the inflation period;
- deflating the cuff over a deflation period;
- obtaining a second set of data during at least a portion of the deflation period; and
- using a processor to determine a first hemodynamic parameter based on the first set of data and the second set of data;
- wherein the first set of data comprises a first oscillometric pulse envelope curve and the second set of data comprises a second oscillometric pulse envelope curve.

14. The method of claim 13, wherein the first hemodynamic parameter is selected from the group consisting of blood pressure, heart rate, aortic index, augmentation index, reflected wave ratio, and mean arterial pressure.

15. The method of claim 13, further comprising determining a second hemodynamic parameter.

16. The method of claim 15, further comprising determining the second hemodynamic parameter based, at least in part, on the first hemodynamic parameter.

17. A system for monitoring a patient, comprising:
- a cuff configured to inflate to at least partially occlude an artery of the patient;
- a cuff controller configured to control inflation and deflation of the cuff;
- a sensor configured to receive a signal associated with the at least partially occluded artery and generate an output signal based on the received signal;
- a signal analysis module configured to receive the output signal and determine a first hemodynamic parameter based on a first set of data obtained during inflation of the cuff and a second set of data obtained during deflation of the cuff; and
- an accelerometer configured to receive a first accelerometer signal corresponding to the first set of data and a second accelerometer signal corresponding to the second set of data;
- wherein the first set of data comprises a first oscillometric pulse envelope curve and the second set of data comprises a second oscillometric pulse envelope curve.

18. The system of claim 17, wherein the signal analysis module is further configured to determine the presence of an irregular signal in the first accelerometer signal and the second accelerometer signal.

19. The system of claim 18, wherein the signal analysis module cancels the determination of the first hemodynamic parameter based upon the presence of an irregular signal.

* * * * *